United States Patent
Liedtke et al.

(10) Patent No.: US 7,030,288 B2
(45) Date of Patent: *Apr. 18, 2006

(54) CONFORMABLE WOUND DRESSING

(75) Inventors: Wayne L. Liedtke, Stillwater, MN (US); Richard L. Jacobson, Oakdale, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/026,177

(22) Filed: Dec. 30, 2004

(65) Prior Publication Data

US 2005/0113733 A1 May 26, 2005

Related U.S. Application Data

(63) Continuation of application No. 10/370,249, filed on Feb. 19, 2003, now Pat. No. 6,838,589.

(51) Int. Cl.
A61F 13/00 (2006.01)

(52) U.S. Cl. ............................ 602/58; 602/42; 602/43; 602/54; 602/57

(58) Field of Classification Search ............ 602/41–59; 206/440, 441; 128/888, 889, 893, 894; 604/304–308; D24/289
See application file for complete search history.

(56) References Cited

U.S. PATENT DOCUMENTS

| RE24,906 E | 12/1960 | Ulrich ............................ 206/59 |
|---|---|---|
| 3,389,827 A | 6/1968 | Abere et al. .................... 220/53 |
| 3,529,597 A | 9/1970 | Fuzak .......................... 128/157 |
| 3,971,374 A | 7/1976 | Wagner ........................ 128/155 |
| 4,112,213 A | 9/1978 | Waldman ...................... 526/279 |
| 4,310,509 A | 1/1982 | Berglund et al. .............. 424/28 |
| 4,323,557 A | 4/1982 | Rosso et al. ................... 424/28 |
| 4,472,480 A | 9/1984 | Olson .......................... 428/332 |
| 4,614,183 A | 9/1986 | McCracken et al. ......... 128/132 |
| 4,619,253 A | 10/1986 | Anhauser et al. ........... 218/156 |
| 4,737,410 A | 4/1988 | Kantner ....................... 428/343 |
| 4,738,257 A | 4/1988 | Meyer et al. ................ 128/156 |
| 5,088,483 A | 2/1992 | Heinecke ...................... 602/46 |
| 5,160,315 A | 11/1992 | Heinecke et al. .............. 602/57 |
| 5,429,592 A | 7/1995 | Jensen .......................... 602/59 |
| 5,505,958 A | 4/1996 | Bello et al. .................. 424/449 |
| 5,531,855 A | 7/1996 | Heinecke et al. ............ 156/252 |
| 5,622,711 A | 4/1997 | Chen .......................... 424/445 |
| 5,633,010 A | 5/1997 | Chen .......................... 424/448 |
| 5,683,354 A | 11/1997 | Levy ............................ 602/54 |
| 5,704,905 A | 1/1998 | Jensen et al. ................. 602/58 |
| 5,738,642 A | 4/1998 | Heinecke et al. .............. 602/58 |
| 5,820,578 A | 10/1998 | Johansen ...................... 602/57 |
| 5,827,213 A | 10/1998 | Jensen ......................... 602/62 |
| D408,541 S | 4/1999 | Dunshee et al. ........... D24/189 |
| 5,902,260 A | 5/1999 | Gilman et al. ................ 602/57 |
| 5,998,694 A | 12/1999 | Jensen et al. ................. 602/57 |

(Continued)

FOREIGN PATENT DOCUMENTS

EP    0 303 422 A2    2/1989

(Continued)

Primary Examiner—Kim M. Lewis
(74) Attorney, Agent, or Firm—Nancy M. Lambert

(57) ABSTRACT

A wound dressing comprising an absorbent pad, an adhesive layer, and a backing layer is described, along with a dressing support layer configured to retain and deliver the wound dressing to a wound, the dressing support layer having a radial configuration that forms a plurality of alternating covered and uncovered portions of the backing layer along the perimeter of the wound dressing.

30 Claims, 4 Drawing Sheets

U.S. PATENT DOCUMENTS

| | | | |
|---|---|---|---|
| 6,169,224 B1 | 1/2001 | Heinecke et al. | 602/58 |
| 6,264,976 B1 | 7/2001 | Heinecke et al. | 424/443 |
| D480,144 S | 9/2003 | Adams et al. | D24/189 |
| D484,601 S | 12/2003 | Griffiths et al. | D24/189 |
| D493,230 S | 7/2004 | Liedtke et al. | D24/189 |
| 6,838,589 B1 * | 1/2005 | Liedtke et al. | 602/58 |
| D503,982 S | 4/2005 | Liedtke et al. | D24/189 |
| 2003/0088202 A1 | 5/2003 | Gilman | 602/46 |

FOREIGN PATENT DOCUMENTS

WO    WO 97/07760 A1    3/1997

* cited by examiner

CONFORMABLE WOUND DRESSING

CROSS REFERENCE TO RELATED APPLICATION

This application is a continuation of U.S. patent application Ser. No. 10/370,249, filed Feb. 19, 2003, now U.S. Pat. No. 6,838,589.

FIELD OF THE INVENTION

The invention relates to wound dressings, and more particularly to a thin film composite dressing and a radial support delivery system.

BACKGROUND OF THE INVENTION

Wound dressings using an absorbent central area surrounded by a larger adhesive film are known. For example, U.S. Pat. No. 5,738,642 (the '642 patent) shows a wound dressing and delivery system comprising a thick absorbent pad placed in the center of a thin backing. A carrier frame surrounds the perimeter of the wound dressing, providing sufficient support (e.g. rigidity) to the backing to facilitate handling of the dressing during application to a wound. The dressing taught in the '642 patent is useful for application to a large variety of wounds. However, a need remains for a wound dressing that can be more effectively applied to irregular surfaces, such as a heel or shoulder. Currently, wound dressings are sometimes cut toward their center to make a cone shaped dressing, but these dressings have significant limitations, including the risk of infection along the line of the cut line, difficulty in applying with one hand, and leakage of fluids from the wound along the cut line.

Therefore, a need remains for an improved wound dressing configured for application to a rounded or other irregularly shaped body part.

SUMMARY OF THE INVENTION

The present invention provides a wound dressing having a thin, flexible periphery and delivery system that facilitates handling the wound dressing. The wound dressing is constructed so as to have improved adhesion to irregular shaped surfaces, such as a heel, and to permit easy application to the irregular shaped surfaces. The wound dressing and delivery system are well suited to positioning an absorbent pad onto a concave or convex surface. For example, the wound dressing and delivery system are suitable for applying an absorbent pad to the heel of a foot, while maintaining an intact sterile perimeter around the wound dressing.

In certain implementations the wound dressing and delivery system include a wound dressing comprising an adhesive layer on a backing layer. Optionally, an absorbent pad or material is applied or attached to the adhesive layer. A dressing support layer is positioned on top of the backing layer, and is configured to retain and deliver the wound dressing to a wound. In particular, the dressing support layer has a radial configuration of extensions that support the backing layer along the perimeter of the wound dressing, while also allowing the dressing to be easily applied to convex surfaces and other non-planer surfaces.

These and various other advantages and features characterizing the invention are pointed out with particularity in the claims annexed hereto and forming a part hereof. However, for a better understanding of the invention, its advantages, and objects obtained by its use, reference should be made to the accompanying drawings and descriptive matter, in which embodiments of the invention are illustrated and described.

BRIEF DESCRIPTION OF THE DRAWINGS

The invention will be further described with reference to the drawings, wherein corresponding reference characters indicate corresponding parts throughout the several views, and wherein.

Figure 1:
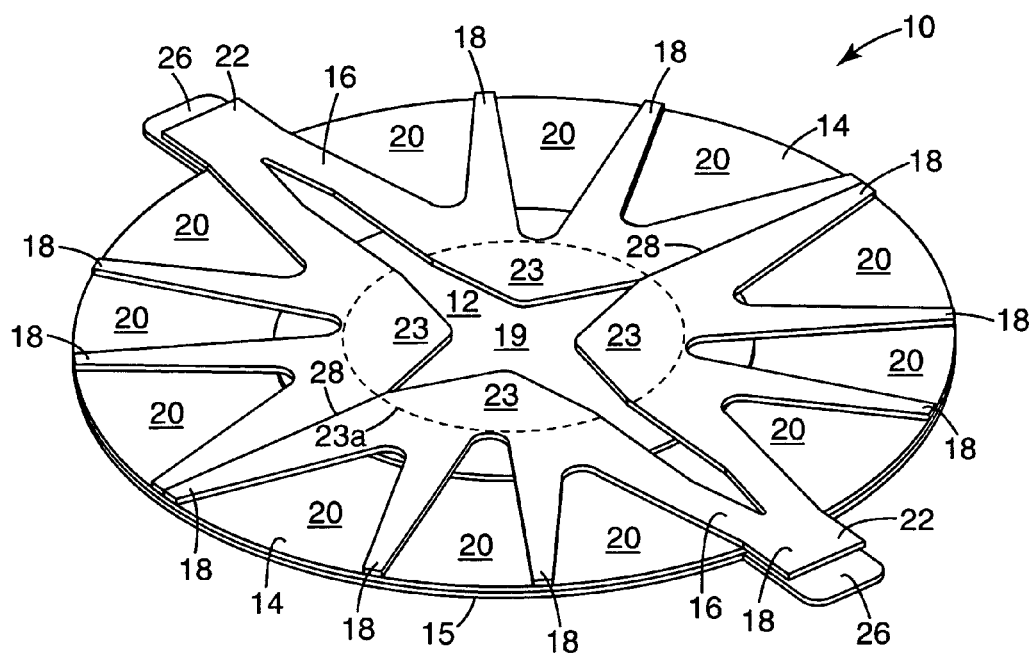
FIG. 1 is a top perspective view of a wound dressing configured and arranged in accordance with an implementation of the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is directed to a wound dressing and delivery system, as well as to methods of applying the wound dressing and delivery system to a patient. The wound dressing and delivery system are particularly well suited to application over a convex surface of a patient, such as a patient's heel. The wound dressing permits a highly absorbent material to be placed against the wound, while the delivery system aids in forming a seal around the convex or irregularly shaped area surrounding the wound.

In some implementations the wound dressing comprises an absorbent pad, a backing layer, and an adhesive layer on the backing layer facing the absorbent pad. The adhesive layer and backing layer form a perimeter around the absorbent pad and hold the absorbent pad in place on a wound. The perimeter formed by the adhesive layer and backing layer keeps the absorbent pad properly positioned, and also helps maintain a sterile environment around the wound. The adhesive layer and backing layer are typically extremely thin, and generally very flexible. If the adhesive layer and backing layer are not properly supported during application they can easily fold over and adhere to themselves, preventing proper application over a wound. The delivery system of the invention provides an easy and effective way to apply the wound dressing to a patient while effectively supporting the perimeter of the dressing to prevent excessive undesirable folding, while allowing controlled, limited folding of the backing layer sufficient to properly contact the patient's uneven skin surface.

Figure 2:
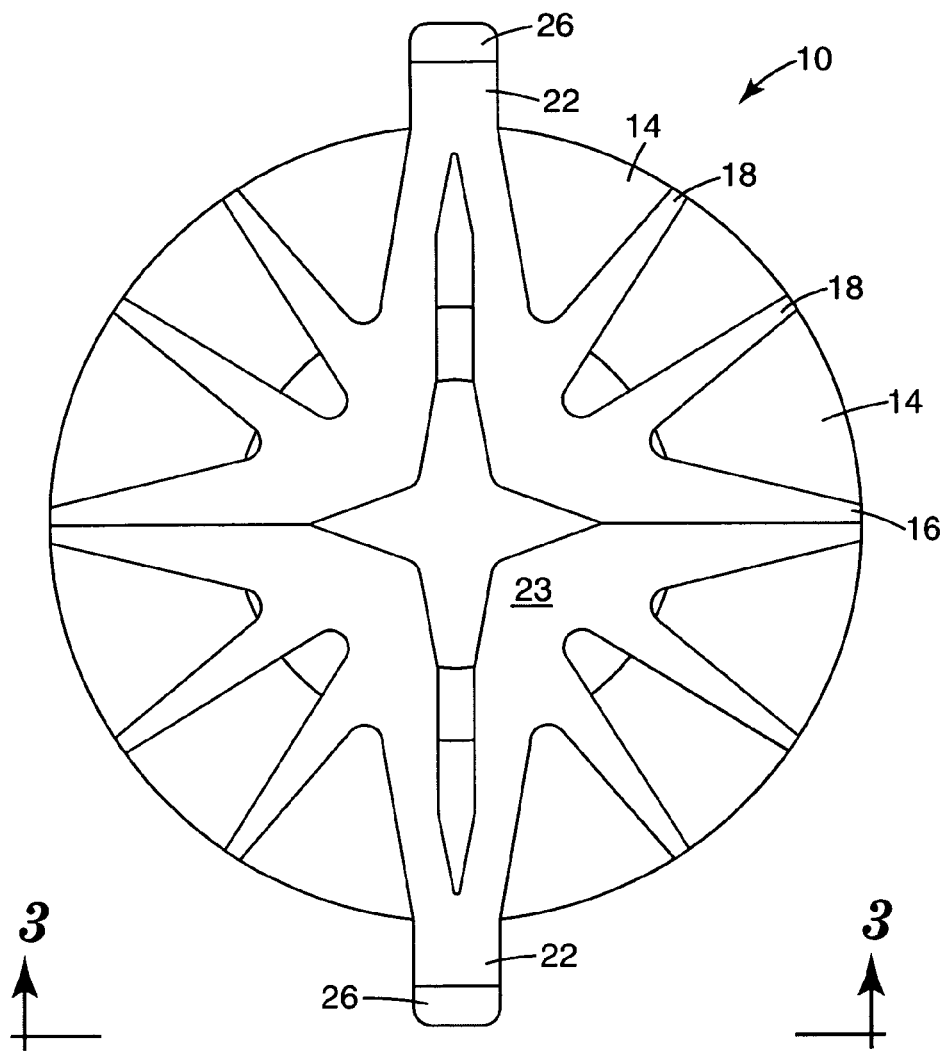
FIG. 2 is a top plan view of the wound dressing of FIG. 1.

FIGS. 1 and 2 show an example of a wound dressing and delivery system made in accordance with the invention. The wound dressing 10 includes a centrally located absorbent pad 12. The absorbent pad 12 is covered by an adhesive layer 17 on a backing layer 14 that extends out to the perimeter 15 of the wound dressing 10. The backing layer 14 is typically extremely thin, flexible, and either transparent or translucent, allowing the absorbent pad 12 to be viewed through it. The delivery system of this invention is particularly useful in connection with a wound dressing 10 having a relatively heavy or stiff absorbent pad 12 positioned on a highly conformable backing layer 14 that is light and flexible relative to the pad 12.

At least one dressing support layer 16 is positioned over the wound dressing 10. In certain implementations of the invention the dressing support layer 16 has a substantially radial configuration, with a plurality of extensions 18 radiating generally from the center 19 of the dressing 10. The support layer 16 forms a plurality of alternating uncovered portions 20 of the adhesive backing layer 14, separated from one another by the extensions 18 along the adhesive perimeter 15 of the wound dressing. The support layer 16 can be a single piece of material, such as a polymeric film, or can be two or more distinct pieces. The support layer 16 shown in FIGS. 1 and 2 is two separate pieces divided by joint 28.

In most implementations the support layer 16 comprises a plurality of extensions 18 radiating from the interior of the dressing 10 toward its edges. The radial configuration of the dressing support layer 16 allows the perimeter 15 of the dressing 10 to be pressed around a convex surface. During application, the uncovered portions 20 of the backing layer 14 between the extensions 18 can contract to maintain a good seal around the edges of the wound. This contraction is typically localized so that individual portions 20 will contract and even fold upon themselves. However, folds or contact between the portions 20 is minimized. In this manner, the wound dressing 10 can have a relatively even, smooth edge without major flaps of the backing layer 14 folded over onto itself.

In some implementations, such as those shown in FIGS. 1 and 2, at least sonic of the plurality of extensions 18 narrow as they approach the perimeter 15 of the dressing 10. Also, in some implementations the dressing support layer 16 comprises at least one portion that extends beyond the edge of the backing layer 14 of the wound dressing 10 to form a tab 22. The tab 22 can be held during positioning of the wound dressing 10. In some implementations, such as those shown in FIGS. 5, 6, and 7, at least some of the plurality of extensions 18 widen as they approach the perimeter 15 of the dressing 10.

In addition, the wound dressing 10 typically includes a carrier film 24, also having a tab 26. The carrier film 24 covers the surface of the wound dressing applied to the patient, generally making contact with the absorbent pad 12 and the periphery of the adhesive layer 17. The carrier film 24 remains attached to wound dressing 10 until a user is ready to apply the dressing. The carrier film 24 may be a single piece or multiple piece release liner, and may be part of or laminated to the package (not shown) containing the dressing, or merely enclosed along with the dressing within the package. The carrier film 24 keeps the adhesive clean during storage and shipping of the wound dressing 10.

In the implementation shown in FIGS. 1 and 2, the extensions 18 converge on the center 19 of the wound dressing 10 but do not cover the center 19. In general, the perimeter of the dressing support layer 16 is releasably adhered to the backing layer 14, but at least part of the center portion 19 of the dressing support layer 16 is not adhered to the backing layer 14. This results in the formation of a plurality of centrally located tabs 23 configured for removing the dressing support layer from the backing layer after the dressing 10 has been applied to a patient. In some embodiments, at least part of the center of the dressing support layer 16 is prevented from adhering to the backing layer 14 by means of a liner 23a on the side of dressing support layer 16 facing backing layer 14. This liner 23a also aids in removal of the support layer, and in some embodiments assists in elevating the tabs 23 when the dressing 10 is applied to a wound.

Figure 3:
FIG. 3 is a side schematic view of the dressing of FIGS. 1 and 2 taken substantially along line 3—3 of FIG. 2.
Figure 4:
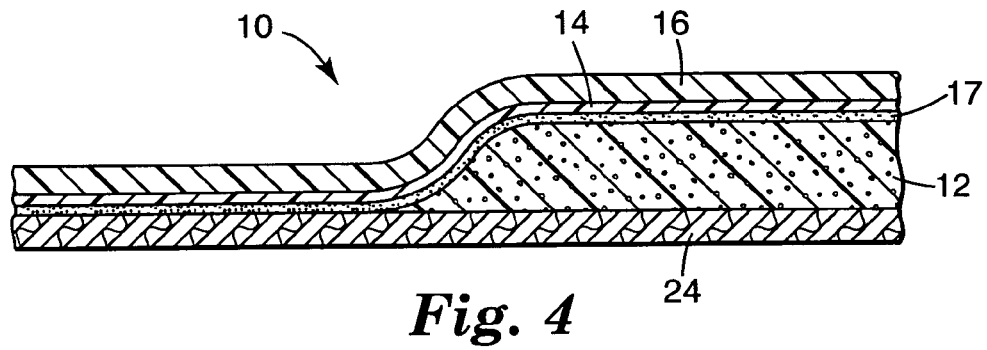
FIG. 4 is an enlarged side cross-sectional view of the dressing of FIG. 3, the cross section taken along the line 4—4 of FIG. 5.

In reference now to FIGS. 3 and 4, a side elevational view of the wound dressing 10 from FIGS. 1 and 2 is depicted in FIG. 3, while FIG. 4 is a cross section of a wound dressing 10 made in accordance with the invention, taken along lines 4—4 of FIG. 3. This cross section shows an absorbent pad 12 that is covered by a thin, flexible backing layer 14, which in turn is partially covered by support layer 16 and adhesive layer 17. FIG. 3 shows important aspects of one implementation of the invention. However, various other implementations are appropriate in order to add or take away from the aspects shown in FIG. 4. For example, the backing layer 14 can be multiple films or coatings without diverging from the invention or deviating from the meaning of the term "film" as used herein. Similarly, the absorbent pad 12 can include multiple sub-layers, including films, webs, sheets, etc. Also, additional layers and films of other materials can be added between the materials described herein without deviating from the invention.

The number of exposed areas 20 of backing layer 14 along the perimeter 15 of the wound dressing 10 can vary in number, shape, and size. However, typically there are at least six distinct exposed areas, generally at least eight, and more commonly twelve or more distinct areas. In some implementations less than 80 percent of the periphery (that portion outside of the absorbent) of the backing layer 14 is covered by the support layer 16, while in other implementations less than 60 percent of the periphery of the backing layer 14 is covered by the support layer 16, while in yet other implementations less than 40 percent of the periphery of the backing layer 14 is covered by the support layer 16.

Figure 7:
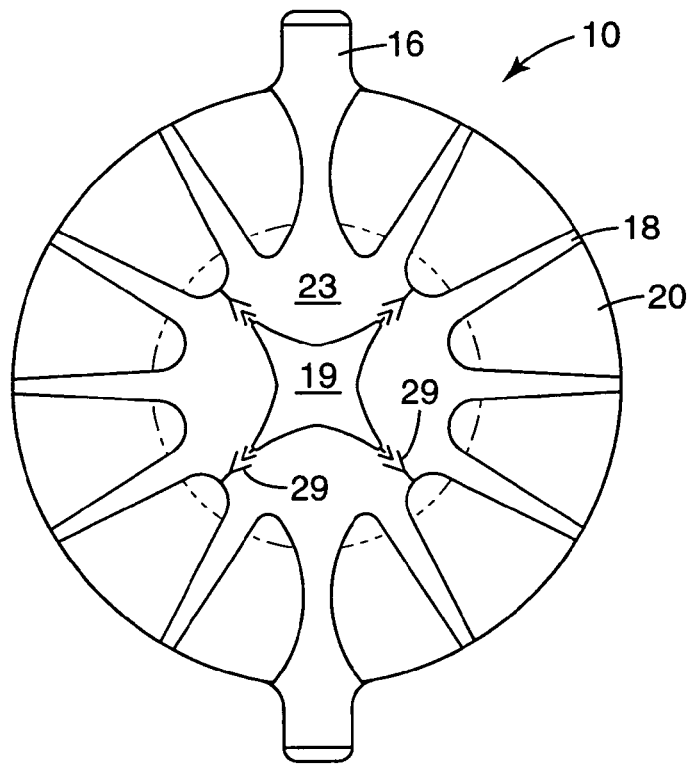
FIG. 7 is a top plan view of yet another alternative embodiment of a wound dressing made in accordance with the invention.

In some embodiments, separation of the extensions 18 is provided by precut paths or lines dividing extensions 18, such as joint 28 shown in FIGS. 1 and 2. In another embodiment, represented in FIG. 7, lines or paths 29 are included between extensions 18. Paths 29 provide controlled tear of the dressing support layer 16 when tabs 23 are lifted to remove the dressing support layer 16 during and/or after application of the dressing 10 to a patient. However, alternative configurations are possible including but not limited to linear, angled, Y-shaped, dual-angled offset, circular holes, and alternating combinations thereof. In FIG. 7, path 29 is shown with a plurality of perforations in an arrow configuration.

The wound dressing 10 is typically applied to a patient by first cleaning the wound and making sure the area around the wound is ready to receive a dressing. The carrier film 24 is then removed from the dressing, exposing the bottom of the absorbent pad 12 and the perimeter of the adhesive layer 17 and the backing layer 14. This perimeter of the backing layer 14 is maintained in a generally planer or stretched orientation by the numerous extensions 18 in the support layer 16. The center of the absorbent pad 12 is brought in contact with the wound, and then the edges of the dressing 10 are gently and smoothly pressed against the patient, thereby bringing the exposed adhesive perimeter of the backing layer 14 in contact with the patient. Generally the areas 20 of the backing layer 14 intermediate the extensions 18 contract to conform around the skin surface. When applied to convex surfaces, the contractions can cause the tabs 23 to rise off the surface of the backing layer 14. After the dressing 10 is properly in position and adhered to a patient's skin, the support layer 16 can be removed. Generally removal of support layer 16 is accomplished by grasping tabs 23 and then using a peeling motion toward the edges of the dressing 10 to remove the support layer 16.

Pressure sensitive adhesive layer 17 is generally provided on one major surface of the backing layer 14 in order to make it adhesive, and a low adhesion coating (low adhesion backsize or LAB) is provided on the other major surface of the backing layer 14 on the side that comes in contact with the support layer 16. The low adhesion coating reduces the need to change the dressing 10 due to unwanted dressing removal when other tapes or devices are placed on the dressing 10 and removed, and reduces the surface friction of the dressing 10 on linen or other fabrics, thereby offering additional protection against the accidental removal of dressing 10. A description of a low adhesion backing material suitable for use with the present invention can be found in U.S. Pat. Nos. 5,531,855 and 6,264,976, which are compatible with a heat seal bond described below, and are incorporated herein in their entirety.

When the support layer 16 is removed from the backing layer 14, the force applied to the edge of the backing layer 14 is generally perpendicular to the perimeter of the dressing 10. This force contrasts with peel forces of conventional support layers, which are parallel to the perimeter of the wound dressing, and which often lift the perimeter off the surface of the patient, potentially loosening the dressing or creating a path for leakage of fluids from the wound.

The absorbent pad 12 of dressing 10 is sometimes referred to as an "island pad" because the backing layer 14 extends substantially beyond the absorbent pad 12, typically beyond the entire periphery of the absorbent pad 12. For example, the length and width of the absorbent pad can be 6 cm by 6 cm, while a backing for this pad can be 9 cm by 9 cm. The pressure sensitive adhesive layer 17 on the peripheral portion of the backing layer 14 is thus not supported or reinforced by the relatively heavy and stiff absorbent pad 12, and absent the benefits of dressing support layer 16 would be difficult to handle without folding, wrinkling or otherwise adhering to itself, rather than adhering to the skin, before and during application.

The support layer 16 is preferably attached to the second major surface of the backing layer 14 (over the low adhesion backing). The bond between the support layer 16 and the backing layer 14 is stronger than the bond between the pressure sensitive adhesive 17 and the carrier layer 24 so that the backing layer 14 remains attached to the support layer 16 when the carrier layer 24 is removed from the dressing 10. Once the carrier layer 24 and dressing 10 are separated, only the support layer 16 and absorbent pad 12 provide significant rigidity to the backing layer 14.

The absorbent pad 12 can comprise a hydrocolloid and hydrogel pad having a thickness of at least 1 mm (e.g., most preferably 3–9 mm), and the backing layer 14 can comprise a transparent elastic polymeric film (e.g., urethane) having a thickness no greater than 0.1 mm (e.g., most preferably 0.021–0.051 mm). It will be appreciated that in this embodiment the absorbent pad 12 is much thicker, stiffer and heavier than the backing layer 14.

Figure 5:
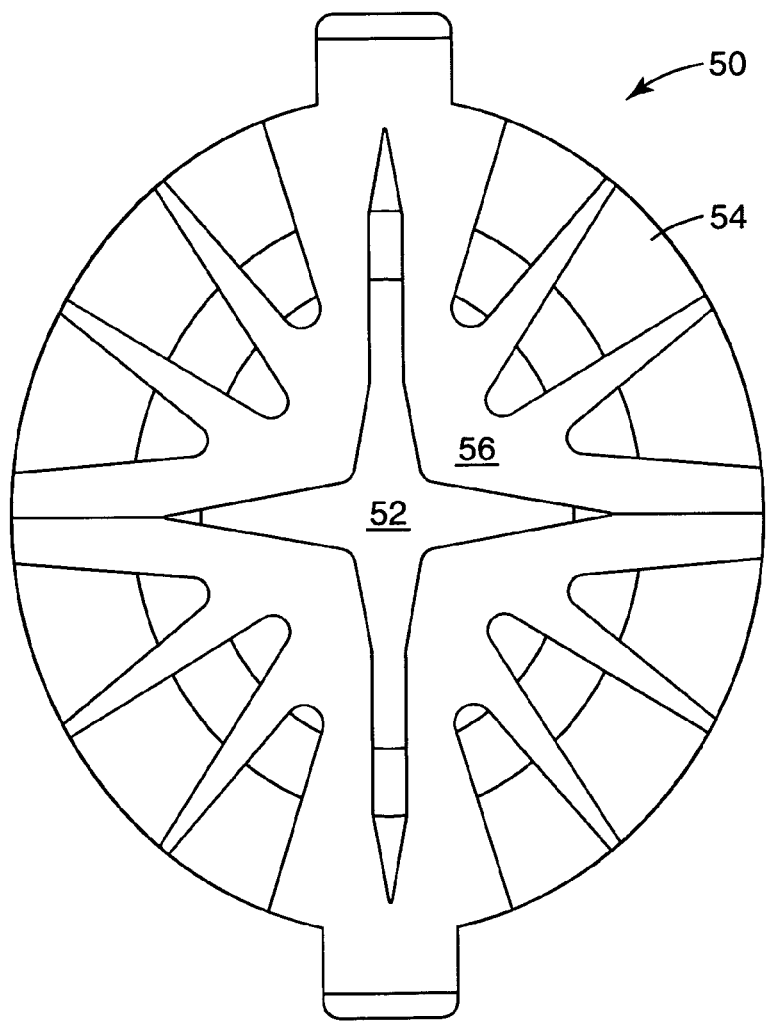
FIG. 5 is a top plan view of an alternative embodiment of a wound dressing made in accordance with the invention.
Figure 6:
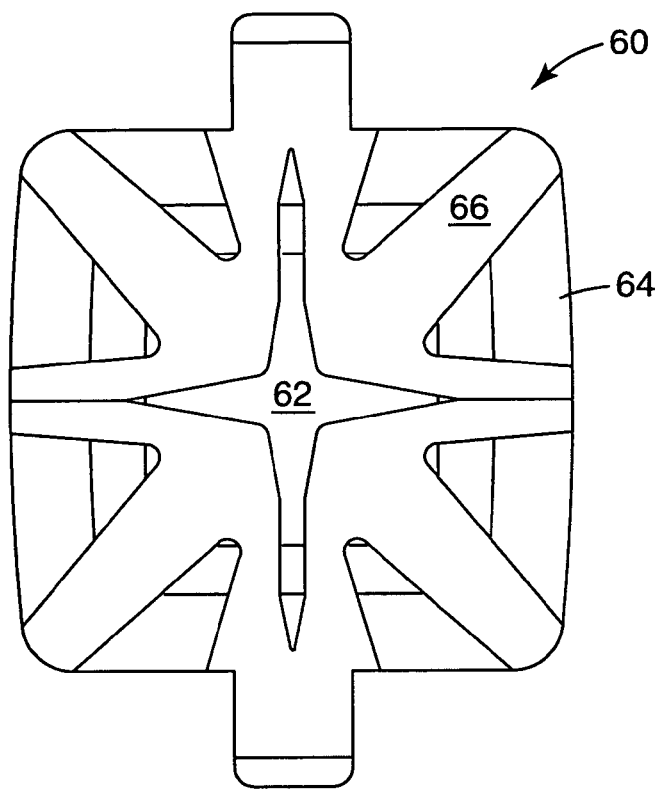
FIG. 6 is a top plan view of another alternative embodiment of a wound dressing made in accordance with the invention.

In reference now to FIGS. 5, 6, and 7, alternative wound dressing implementations are shown. In FIGS. 5 and 6, different shapes for the wound dressings are shown. The embodiment shown in FIG. 5 is an oval shaped wound dressing 50 with an absorbent pad 52, adhesive backing 54, and support 56. The embodiment shown in FIG. 6 is a square shaped wound dressing 60 with an absorbent pad 62, adhesive backing 64, and support 66. In FIG. 7, the various portions of the support layer are shown connected by a tear path of perforations.

Additional aspects of various components of the invention will now be described in greater detail.

Absorbent Pad

Absorbent pad 12 can be manufactured of any of a variety of materials including, but not limited to, woven or nonwoven cotton or rayon. Absorbent pad 12 is useful for containing a number of substances, optionally including antimicrobial agents, drugs for transdermal drug delivery, chemical indicators to monitor hormones or other substances in a patient, etc.

The absorbent may include a hydrocolloid composition, including the hydrocolloid compositions described in U.S. Pat. Nos. 5,622,711 and 5,633,010, the disclosures of which are hereby incorporated by reference. The hydrocolloid absorbent may comprise, for example, a natural hydrocolloid, such as pectin, gelatin, or carboxymethylcellulose (CMC) (Aqualon Corp., Wilmington, Del.), a semi-synthetic hydrocolloid, such as cross-linked carboxymethylcellulose (X4ink CMC) (e.g. Ac-Di-Sol; FMC Corp., Philadelphia, Pa.), a synthetic hydrocolloid, such as cross-linked polyacrylic acid (PAA) (e.g., CARBOPOL™ No. 974P; B.F. Goodrich, Brecksville, Ohio), or a combination thereof. Generally, the hydrocolloid absorbent component comprises from about 5 percent to about 60 percent by weight of the absorbent composition. When preparing an absorbent composition for use in a wound dressing the hydrocolloid absorbent preferably comprises from about 20 percent to about 40 percent by weight of the composition. Absorbent materials may also chosen from other synthetic and natural hydrophilic materials including polymer gels and foams.

Backing Materials

Suitable backing materials for backing layer 14 include, for example, nonwoven fibrous webs, woven fibrous webs, knits, films and other familiar backing materials. The backing materials are typically translucent or transparent polymeric elastic films. The backing can be a high moisture vapor permeable film backing. U.S. Pat. No. 3,645,835, the disclosure of which is hereby incorporated by reference, describes methods of making such films and methods for testing their permeability.

The backing advantageously should transmit moisture vapor at a rate equal to or greater than human skin. In some embodiments, the adhesive coated backing layer transmits moisture vapor at a rate of at least 300 $g/m^2/24$ $hrs/37°$ C./100–10% RH, frequently at least 700 $g/m^2/24$ $hrs/37°$ C./100–10% RH, and most typically at least 2000 $g/m^2/24$ $hrs/37°$ C./100–10% RH using the inverted cup method.

The backing layer 14 is generally conformable to anatomical surfaces. As such, when the backing layer 14 is applied to an anatomical surface, it conforms to the surface even when the surface is moved. The backing layer 14 is also conformable to animal anatomical joints. When the joint is flexed and then returned to its unflexed position, the backing layer 14 can be made such that it stretches to accommodate the flexion of the joint, but is resilient enough to continue to conform to the joint when the joint is returned to its unflexed condition.

A description of this characteristic of backing layers 14 for use with the present invention can be found in issued U.S. Pat. Nos. 5,088,483 and 5,160,315, the disclosures of which are hereby incorporated by reference in their entirety. Specific suitable backing materials are elastomeric polyurethane, co-polyester, or polyether block amide films. These films combine the desirable properties of resiliency, high moisture vapor permeability, and transparency found in backings.

Support Layer

The material used to form the support layer 16 is generally substantially more rigid than the backing layer 14 to prevent the backing layer 14 from improperly wrinkling during application to a patient. The support layer 16 can be heat-sealable to the backing layer 14 with or without a low adhesion coating described above. In general, the support layer materials can include, but are not limited to, polyethylene/vinyl acetate copolymer-coated papers and polyester films. One example of a suitable support layer material is a polyethylene/vinyl acetate copolymer coated super calendared Kraft paper (1-80BKG-157 PE; DCP-Lohya of Dixon, Ill.).

The support layer 16 can include perforations to aid in separating portions of the support layer 16 after application of the dressing 10 in a patient. Spacing and shape of the perforations are adjusted to give a support layer with relatively easy to tear performance on removal of the support layer from the applied dressing. The perforations may be shaped in accordance with any of the accepted perforation patterns including linear, angled, Y-shaped, V-shaped, dual-angled offset, sinusoidal, etc.

Pressure Sensitive Adhesive

Various pressure sensitive adhesives can be used to form adhesive layer 17 on the backing layer 14 to make it adhesive. The pressure sensitive adhesive is usually reasonably skin compatible and "hypoallergenic", such as the acrylate copolymers described in U.S. Pat. No. RE 24,906, the disclosure of which is hereby incorporated by reference. Particularly useful is a 97:3 iso-octyl acrylate: acrylamide copolymer, as is 70:15:15 isooctyl acrylate: ethyleneoxide acrylate: acrylic acid terpolymer described in U.S. Pat. No. 4,737,410, the disclosure of which is hereby incorporated by reference is suitable. Additional useful adhesives are described in U.S. Pat. Nos. 3,389,827, 4,112,213, 4,310,509, and 4,323,557, the disclosures of which are hereby incorporated by reference. Inclusion of medicaments or antimicrobial agents in the adhesive is also contemplated, as described in U.S. Pat. Nos. 4,310,509 and 4,323,557, both of which are also hereby incorporated by reference.

Carrier Films

Carrier films 24 suitable for use with the invention can be made of kraft papers, polyethylene, polypropylene, polyester or composites of any of these materials. The films are preferably coated with release agents such as fluorochemicals or silicones. For example, U.S. Pat. No. 4,472,480, the disclosure of which is hereby incorporated by reference, describes low surface energy perfluorochemical liners. The liners are papers, polyolefin films, or polyester films coated with silicone release materials. Examples of commercially available silicone coated release papers are POLYSLIK™, silicone release papers available from Rexam Release (Bedford Park, Ill.) and silicone release papers supplied by DCP-Lohya Co. (Dixon, Ill.).

As various changes could be made in the above constructions, compositions and methods without departing from the scope of the invention as defined in the claims, it is intended that all matter contained in the above description or shown in the accompanying drawings be interpreted as illustrative and not in a limiting sense.

What is claimed is:

1. A wound dressing support system, comprising:
a wound dressing comprising a backing layer; and
a wound dressing support layer comprising a radial configuration that forms a plurality of alternating covered and uncovered portions along the perimeter of a wound dressing when attached to the backing layer of the wound dressing.

2. The wound dressing support system of claim 1, wherein the support layer comprises a plurality of extensions radiating from the interior of the dressing toward the edges of the dressing.

3. The wound dressing support system of claim 2, wherein a path of separation is located between at least two adjacent extensions.

4. The wound dressing support system of claim 3 wherein the path of separation comprises a plurality of perforations.

5. The wound dressing support system of claim 2, wherein at least some of the plurality of extensions widen as they approach the edge of the dressing.

6. The wound dressing support system of claim 2, wherein the dressing support layer comprises at least one portion that extends beyond the edge of the backing layer of the wound dressing.

7. The wound dressing support system of claim 6, wherein the portion that extends beyond the edge of the backing layer is configured to be held during positioning of the wound dressing.

8. The wound dressing support system of claim 2, wherein the extensions converge on the center of to wound dressing but do not cover the center of the dressing.

9. The wound dressing support system of claim 2, wherein the extensions are flexible.

10. The wound dressing support system of claim 1, wherein the dressing support layer comprises at least two portions extending beyond the edge of the backing layer to aid in positioning of the dressing.

11. The wound dressing support system of claim 1, wherein the perimeter of the dressing support layer is releasably adhered to backing layer, but at least part of a center portion of the dressing support layer proximate the center of the dressing is not adhered to the backing layer.

12. The wound dressing support system of claim 1, further comprising a plurality of centrally located tabs configured for removing the dressing support layer from the backing layer after the dressing has been applied to a patient.

13. The wound dressing support system of claim 1, wherein the support layer covers less than 80 percent of the perimeter of the wound dressing.

14. The wound dressing support system of claim 1, wherein the support layer coven less than 60 percent of the perimeter of the wound dressing.

15. The wound dressing support system of claim 1, wherein the support layer covers less than 40 percent of the perimeter of the wound dressing.

16. The wound dressing support system of claim 1, wherein to perimeter of the wound dressing comprises at least six distinct uncovered portions of the wound dressing.

17. The wound dressing support system of claim 1, wherein the perimeter of the wound dressing comprises at least six distinct uncovered portions of the wound dressing.

18. The wound dressing support system of claim 1, wherein the wound dressing comprises a transparent or translucent polymeric film.

19. A wound dressing and delivery system comprising:
a wound dressing substrate configured to be placed on a wound; and
a dressing delivery substrate configured to be retained on the wound dressing substrate before placement of the wound dressing substrate on a wound and removed from the wound dressing substrate after it has been applied to the wound;
wherein the delivery substrate has one or more central portions positioned proximate the interior and a plurality of extensions radiating front the one or more central portions toward the periphery of the dressing substrate.

20. The wound dressing and delivery system of claim 19, wherein at least some of the plurality of extensions widen as they approach the edge of the wound dressing substrate.

21. The wound dressing and delivery system of claim 19, wherein the dressing delivery substrate comprises at least two extensions beyond the edge of the wound dressing substrate to aid in positioning of the dressing.

22. The wound dressing and delivery system of claim 19, wherein the extensions converge on the center of the wound dressing but do not cover the center of the dressing.

23. The wound dressing and delivery system of claim 19, wherein the perimeter of the delivery substrate is reversibly adhered to the wound dressing substrate, but at least part of each of the central portions are not adhered to the wound dressing substrate.

24. The wound dressing and delivery system of claim 19, further comprising a plurality of centrally located tabs configured for removing the delivery substrate from the dressing substrate after the dressing has been applied to a patient.

25. The wound dressing and delivery system of claim 19, wherein less than 80 percent of the less absorbent periphery of the wound dressing substrate is covered by the dressing delivery substrate.

26. The wound dressing and delivery system of claim 19, wherein less than 60 percent of the less absorbent periphery of the wound dressing substrate is covered by the dressing delivery substrate.

27. The wound dressing and delivery system of claim 19, wherein less than 40 percent of the less absorbent periphery of the wound dressing substrate is covered by the dressing delivery substrate.

28. The wound dressing and delivery system of claim 19, further comprising a release liner in contact with the wound dressing substrate.

29. The wound dressing and delivery system of claim 19, wherein (he less absorbent periphery of the wound dressing comprises at least six distinct uncovered areas.

30. The wound dressing and delivery system of claim 19, wherein the wound dressing substrate comprises a transparent or translucent polymeric film.

* * * * *

UNITED STATES PATENT AND TRADEMARK OFFICE
CERTIFICATE OF CORRECTION

PATENT NO. : 7,030,288 B2  Page 1 of 1
APPLICATION NO. : 11/026177
DATED : April 18, 2006
INVENTOR(S) : Wayne L. Liedtke It is certified that error appears in the above-identified patent and that said Letters Patent is hereby corrected as shown below:

Column 3
Line 41, Delete "sonic" and insert -- some --, therefore.

Column 8
Line 36, Delete "to" and insert -- the -- therefore.
Line 57, Delete "coven" and insert -- covers --, therefore.
Line 63, Delete "to" and insert -- the --, therefore.

Column 9
Line 14, Delete "front" and insert --from --, therefore.

Column 10
Line 25, Delete "(he" and insert -- the --, therefore.

Signed and Sealed this

Thirty-first Day of July, 2007

JON W. DUDAS
*Director of the United States Patent and Trademark Office*